(12) United States Patent
Byrne

(10) Patent No.: US 10,620,129 B1
(45) Date of Patent: Apr. 14, 2020

(54) SYSTEMS AND METHODS FOR DETERMINING CARBON SYSTEM PARAMETERS OF WATER

(71) Applicant: Robert Howard Byrne, St. Petersburg, FL (US)

(72) Inventor: Robert Howard Byrne, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 250 days.

(21) Appl. No.: 15/782,471

(22) Filed: Oct. 12, 2017

Related U.S. Application Data

(60) Provisional application No. 62/407,849, filed on Oct. 13, 2016.

(51) Int. Cl.
| | |
|---|---|
| *G01N 21/80* | (2006.01) |
| *G01N 21/3577* | (2014.01) |
| *G01N 21/79* | (2006.01) |
| *G01N 33/18* | (2006.01) |
| *G01N 1/28* | (2006.01) |
| *G01J 3/28* | (2006.01) |
| *G01N 21/33* | (2006.01) |

(52) U.S. Cl.
CPC ............... *G01N 21/80* (2013.01); *G01J 3/28* (2013.01); *G01N 1/28* (2013.01); *G01N 21/33* (2013.01); *G01N 21/3577* (2013.01); *G01N 21/79* (2013.01); *G01N 33/1846* (2013.01); *G01J 2003/283* (2013.01); *Y10T 436/235* (2015.01)

(58) Field of Classification Search
CPC .... G01N 21/80; G01N 21/33; G01N 21/3577; G01N 21/79; G01N 1/28; G01N 33/18; G01N 33/1826; G01N 33/1846; G01J 3/28; G01J 2003/283

USPC ....... 436/39, 145, 146, 163, 164; 422/82.05, 422/82.09
See application file for complete search history.

(56) References Cited

U.S. PATENT DOCUMENTS

| | | | | |
|---|---|---|---|---|
| 5,925,572 A | * | 7/1999 | Byrne | ................. G01N 21/272 324/438 |
| 7,842,507 B1 | * | 11/2010 | Byrne | ................. G01N 33/182 436/133 |
| 10,060,891 B1 | * | 8/2018 | Byrne | ................. G01N 31/221 |
| 2006/0234389 A1 | * | 10/2006 | Byrne | ................ G01N 21/0303 436/163 |

(Continued)

OTHER PUBLICATIONS

Wang et al. Analytica Chimica Acta, vol. 596, 2007, pp. 23-36.*
Cuyler et al. Analytica Chimica Acta, vol. 1020, Mar. 10, 2018, pp. 95-103.*

*Primary Examiner* — Maureen Wallenhorst
(74) *Attorney, Agent, or Firm* — Meunier Carlin & Curfman LLC

(57) ABSTRACT

In one embodiment, determining carbon system parameters of water includes measuring the pH of a first subsample of the water using a spectrophotometer, adding nitric acid as a titrant to a second subsample of the water to obtain a titrated subsample, measuring a concentration of added nitric acid in the titrated subsample using a spectrophotometer, measuring the pH of the titrated subsample using a spectrophotometer, and calculating one or more unknown carbon system parameters using the pH of the first subsample, the pH of the titrated subsample, and the concentration of added nitric acid of the titrated subsample.

19 Claims, 3 Drawing Sheets

(56) References Cited

U.S. PATENT DOCUMENTS

2015/0346178 A1\* 12/2015 Wang ................. G01N 33/1886
436/52

\* cited by examiner

SYSTEMS AND METHODS FOR DETERMINING CARBON SYSTEM PARAMETERS OF WATER

CROSS-REFERENCE TO RELATED APPLICATION

This application claims priority to U.S. Provisional Application Ser. No. 62/407,849, filed Oct. 13, 2016, which is hereby incorporated by reference herein in its entirety.

BACKGROUND

To date, the ocean has absorbed about 30% of the anthropogenic carbon dioxide ($CO_2$) emitted since the industrial revolution, thereby causing declining pH and carbonate saturation states ($\Omega$) throughout the surface ocean, i.e., ocean acidification (OA). Research into the impacts of ocean acidification has shown that lower saturation states cause calcification rates to decrease in many calcifying species. Saturation state monitoring is crucial to understanding the diverse impacts of ocean acidification on marine ecosystems and coastal economies in the next century.

The seawater $CO_2$ system can be characterized by observations of the five measurable carbon system parameters: pH, total alkalinity ($A_T$), total dissolved inorganic carbon ($C_T$), $CO_2$ fugacity ($fCO_2$), and total carbonate ion concentration ($[CO_3^{2-}]_T$). Models of carbon system thermodynamics enable the calculation of all carbon system parameters (including calcite and aragonite saturation states) from any two of the measurable variables. For example, the parameter pair of $C_T$ and $A_T$ is used for saturation state calculations. However, measuring $C_T$ and $A_T$ requires two separate instrumental setups and protocols, and both protocols are somewhat complex and time-consuming. Additionally, attaining precise $A_T$ measurements requires meticulous gravimetric or volumetric measurements of the acid added during analytical titrations. This requirement can be especially challenging for shipboard measurements. A simpler, faster, and more convenient method for determining carbon system parameters, such as carbonate saturation state, would be beneficial for the widespread monitoring of ocean acidification.

Previously, indicators have been used to quantify titrant additions without the use of volumetric or gravimetric analysis. For example, seawater alkalinity measurements have been performed using a sulfonephthalein pH indicator dissolved in a hydrochloric (HCl) acid titrant to precisely quantify the concentration of acid that has been added using a spectrophotometer. Unfortunately, using such indicators requires meticulous preparation and characterization of the indicator-acid mixtures. In addition, such indicators can degrade or precipitate over time, thereby skewing results.

From the above discussion, it can be appreciated that it would be desirable to have a simple, fast, and convenient method for determining carbon system parameters of water, such as seawater, that does not require volumetric or gravimetric analysis and that does not require the addition of an indicator to an acid titrant.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
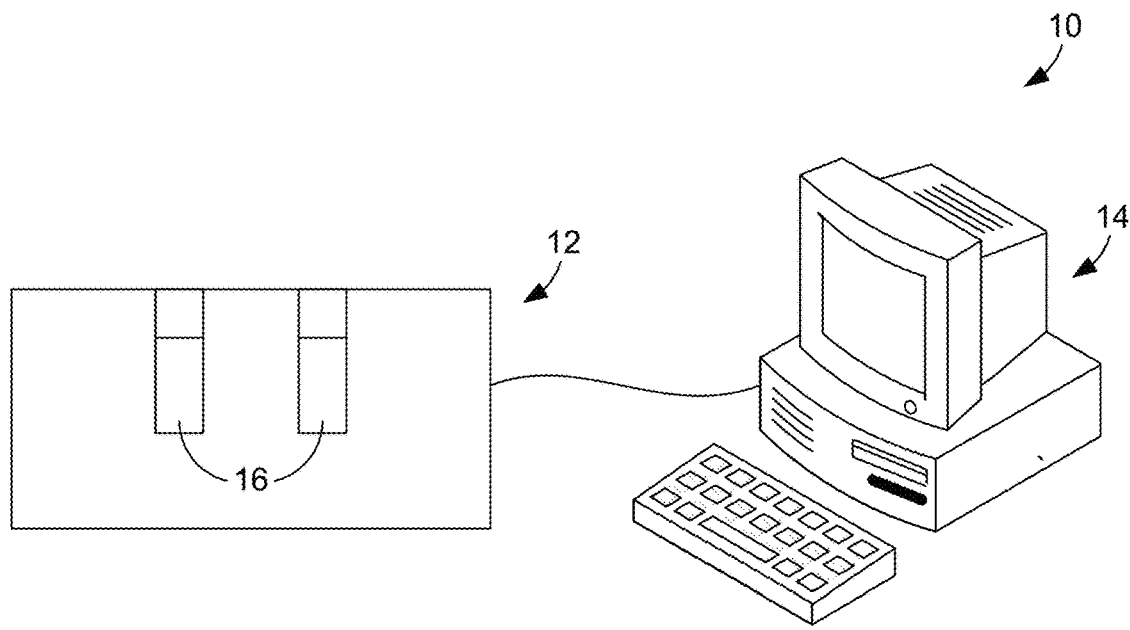
FIG. 1 is a schematic diagram of an embodiment of a system for determining carbon system parameters of water.

As described above, it would be desirable to have a simple, fast, and convenient method for determining carbon system parameters of water, such as seawater, that does not require volumetric or gravimetric analysis and that does not require the addition of an indicator to an acid titrant. Disclosed herein are examples of such systems and methods. In some embodiments, visible and UV absorbances of seawater subsamples are measured in paired spectrophotometric cells. Nitric acid ($HNO_3$) is added to one of the samples as a titrant. Because nitric acid inherently absorbs ultraviolet (UV) light, there is a direct relationship between nitrate concentration and UV absorbance and, therefore, no indicator must be added to the nitric acid titrant to determine the concentration of added acid. This obviates the need for meticulous preparation and calibration of indicator-acid mixtures. Through the spectrophotometric analysis, the pH of each subsample can be measured, as well as the concentration of added nitric acid in the titrated subsample. From these parameters, each unknown carbon system parameter of the seawater, as well as the carbonate saturation state, can be calculated. In some embodiments, the measured parameters can be input into a computer program configured to output the calculated carbon system parameters.

The disclosure that follows begins with a discussion of the theory that underlies the disclosed invention. Described after that discussion are example systems and methods that can be used to determine carbon system parameters. Finally, experiments and the results obtained from the experiments are discussed.

Theory The relationship between total alkalinity ($A_T$) and total dissolved inorganic carbon ($C_T$) in a seawater sample is given as $$A_T = C_T\left(\frac{2 \cdot K_1' \cdot K_2' + K_1' \cdot [H^+]}{K_1' \cdot K_2' + K_1' \cdot [H^+] + ([H^+])^2}\right) + \frac{B_T \cdot K_B'}{K_B' + [H^+]} + \frac{K_W'}{[H^+]} - [H^+] \quad (1)$$

where $K_1'$, $K_2'$, $K_B'$, and $K_W'$ are the dissociation constants of carbonic acid, bicarbonate, boric acid, and water in seawater, respectively, and $B_T$ is the total boron concentration. These variables are expressed in units of moles $kg^{-1}$ (additional terms for nutrients and organic alkalinity are not explicitly shown here). The term $[H^+]$ represents total hydrogen ion concentration, which is obtained from measurements of seawater pH ($pH=-\log[H^+]$).

The disclosed method relies on the use of paired, initially identical seawater subsamples and a one-step titration using nitric acid. Initial conditions of the seawater (subsample 1) are indicated by subscript $_1$, and conditions after a one-step $HNO_3$ addition (subsample 2) are indicated by subscript $_2$. When the $HNO_3$ is added to subsample 2, the initial $A_{T1}$ of the seawater is decreased by an amount equal to the change in $NO_3^-$ concentration ($\Delta NO_3^-$) while $C_T$ and $B_T$ are unchanged. Conditions before and after acidification are related as follows:

$$A_{T2} = \theta \cdot A_{T1} - \Delta NO_3^- = \theta \cdot C_T \left( \frac{2 \cdot K_1' \cdot K_2' + K_1' \cdot [H^+]_2}{K_1' \cdot K_2' + K_1' \cdot [H^+]_2 + ([H^+]_2)^2} \right) + \quad (2)$$

$$\theta \cdot \frac{B_T \cdot K_B'}{K_B' + [H^+]_2} + \frac{K_W'}{[H^+]_2} - [H^+]_2$$

where the dilution factor $\theta$ is given by $$\theta = \frac{V_{sw}}{V_{sw} + V_{HNO3}} \quad (3)$$

$V_{SW}$ is the initial volume of seawater and $V_{HNO3}$ is the volume of added nitric acid. The $\theta$ term accounts for the minor dilution of $A_{T1}$, $C_T$, and $B_T$ caused by the acid addition.

The $\Delta NO_3^-$ term in Eq. (2) can be obtained from spectrophotometric measurements of absorbance A at wavelength $\lambda$, in combination with Beer's Law: $_\lambda A = C \, 1 \,_\lambda \varepsilon$, where C is the concentration of the absorbing analyte, l is the spectrophotometric cell path length, and $_\lambda \varepsilon$ is the molar absorptivity coefficient of the absorbing constituent. The resulting equation is $$\Delta NO_3^- = \frac{_{235}A_{NO3}}{l \cdot _{235}\varepsilon_{NO3} \cdot \rho_{sw}} \quad (4)$$

where $_{235}A_{NO3}$ is the nitrate absorbance at 235 nm, $_{235}\varepsilon_{NO3}$ is the molar absorptivity coefficient of nitrate at 235 nm and 25° C., and $\rho_{sw}$ is the density of the seawater (a function of salinity S and temperature T). Routine baseline corrections applied to the absorbance measurements subtract out the effects of any nitrate initially in the seawater sample. The $\rho_{sw}$ term is required to yield $\Delta NO_3^-$ in the desired concentration units (mole kg).

With spectrophotometric measurements of $pH_1$ and $pH_2$, Eqs. (1) and (2) can be used to calculate $C_T$ and $A_{T1}$ of the original seawater sample. For convenience, the equations can be first simplified by defining the following parameters:

$$f_C = \frac{2 \cdot K_1' \cdot K_2' + K_1' \cdot [H^+]}{K_1' \cdot K_2' + K_1' \cdot [H^+] + ([H^+])^2} \quad (5)$$

$$f_B = \frac{B_T \cdot K_B'}{K_B' + [H^+]} \quad (6)$$

$$f_W = \frac{K_W'}{[H^+]} - [H^+] \quad (7)$$

where $f_C$ is related to carbonate alkalinity, $f_B$ is borate alkalinity, and $f_W$ is hydroxide alkalinity minus the hydrogen ion concentration. The dissociation constants within these functions depend on S, T, and hydrostatic pressure P.

Eq. (1), which applies to the unacidified seawater, can now be written as $$A_{T1} = C_T f_{C1} + f_{B1} + f_{W1} \quad (8)$$

Eq. (2), which applies to the acidified seawater, can be written as $$A_{T2} = \theta A_{T1} - \Delta NO_3^- = \theta C_T f_{C2} + \theta f_{B2} + f_{W2} \quad (9)$$

To obtain the seawater $C_T$ (which is not directly changed by the addition of nitric acid), Eq. (9) can be rearranged and written in a form similar to Eq. (8):

$$A_{T1} = C_T f_{C2} + f_{B2} + \theta^{-1} \Delta NO_3^- + \theta^{-1} f_{W2} \quad (10)$$

By subtracting Eq. (8) from Eq. (10), $A_{T1}$ is eliminated and CT is expressed directly in terms of $f_C$, $f_B$, $f_W$, and $\theta$:

$$C_T(f_{C1} - f_{C2}) = \theta^{-1} \Delta NO_3^- + f_{B2} - f_{B1} + \theta^{-1} f_{W2} - f_{W1} \quad (11)$$

After rearrangement, $C_T$ is given explicitly as $$C_T = \frac{\theta^{-1} \Delta NO_3^- + f_{B2} - f_{B1} + \theta^{-1} f_{W2} - f_{W1}}{f_{C1} - f_{C2}} \quad (12)$$

The total alkalinity of the original seawater solution ($A_{T1}$) can then be calculated using this value of CT (Eq. 12) in Eq. (8).

The carbonate ion concentration ($[CO_3^{2-}]_T$) can be calculated from $C_T$ (Eq. 12), $A_{T1}$ (Eq. 8), and the measured S and in situ T of the seawater sample.

Finally, the carbonate saturation state is calculated from $$\Omega = \frac{[CO_3^{2-}]_T \cdot [Ca^{2+}]_T}{K_{sp}'} \quad (13)$$

where $[Ca^{2+}]_T$ is the total calcium ion concentration, and $K'_{sp}$ is the solubility product of the calcium carbonate polymorph of interest (e.g., calcite or aragonite). The calcium term is calculated from the direct proportionality between calcium and salinity: $[Ca^{2+}]=0.0102821*S/35$. In this disclosure, the focus is on aragonite saturation states because aragonite is the more soluble of the two major calcium carbonate polymorphs.

Example Systems and Methods

From the above analysis, it can be appreciated that the unknown measurable carbon system parameters of the seawater can be determined from pH measurements for the two seawater subsamples and the concentration of added nitric acid (i.e., $\Delta NO_3^-$) in the titrated subsample. More particularly, $pH_1$, $pH_2$, and $\Delta NO_3^-$ can be input into Eqs. (1) and (2) (or the simplified equations derived therefrom) to calculate total alkalinity ($A_T$) and total dissolved inorganic carbon ($C_T$) of the seawater. Once those parameters have been calculated, the carbonate ion concentration ($[CO_3^{2-}]_T$) can be calculated from $C_T$ (Eq. 12), $A_{T1}$ (Eq. 8), and the measured salinity (S) and in situ temperature (T) of the seawater sample. In addition, the $CO_2$ fugacity ($fCO_2$) can be calculated from $A_T$ and $C_T$ using commercially available programs, thereby providing each measurable carbon system parameter. In addition, the carbonate saturation state can be calculated from the total carbonate ion concentration using Eq. 13.

FIG. 1 schematically illustrates an embodiment of a system 10 for determining carbon system parameters of seawater. As shown in FIG. 1, the system 10 generally includes a spectrophotometer 12 that is in electrical communication with a computing device 14. The spectrophotometer 12 is configured to receive two sample cells 16 in which subsamples to be spectrophotometrically analyzed can be contained.

Figure 2:
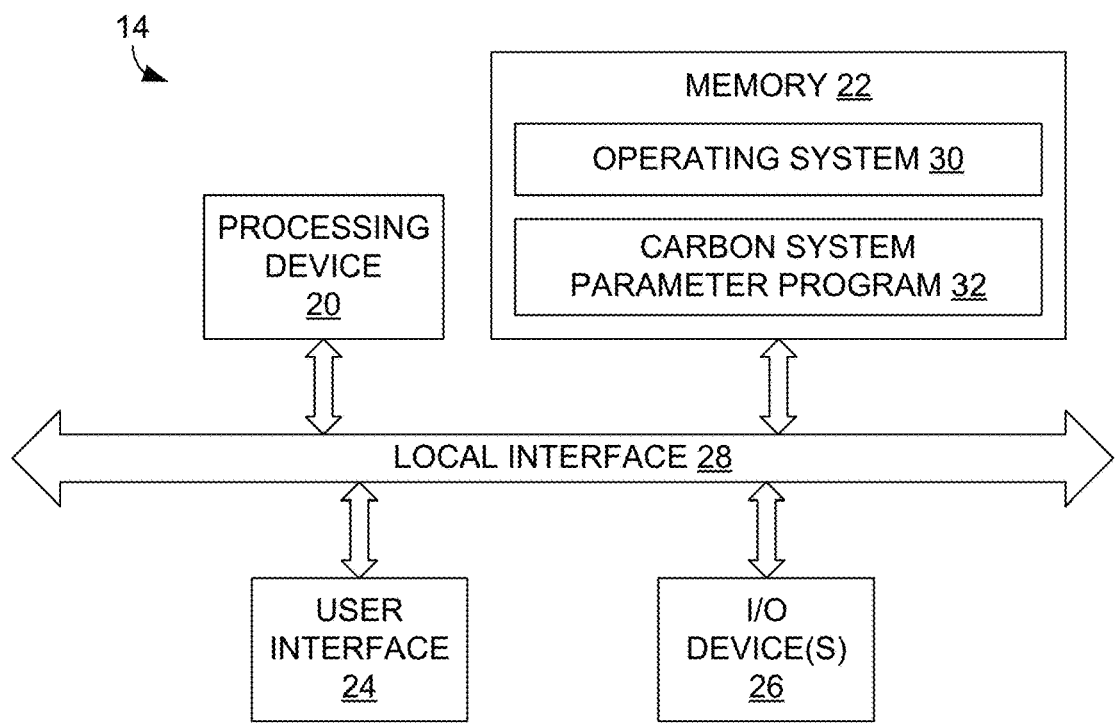
FIG. 2 is block diagram of an embodiment for a computing device shown in FIG. 1.

FIG. 2 illustrates an example architecture for the computing device 14. As shown in this figure, the computing device 14 generally comprises a processing device 20, memory 22, a user interface 24, and I/O devices 26, each of which is connected to a local interface 28. The processing device 20 can include a central processing unit (CPU) or a semiconductor-based microprocessor (in the form of a microchip). The memory 22 (a non-transitory computer-readable medium) includes any one of or a combination of volatile memory elements (e.g., RAM) and nonvolatile memory elements (e.g., hard disk, solid-state drive, etc.). The user interface 24 comprises the components with which a user interacts with the computing device 14 and the I/O devices 26 are adapted to facilitate communication with other devices. The memory 22 comprises programs (i.e., logic) including an operating system 30 and a carbon system parameter program 32 that comprises one or more algorithms (computer-executable instructions) that are configured to receive the data collected by the spectrophotometer 12 and calculate one or more carbon system parameters. In some embodiments, the carbon system parameter program 32 comprises algorithms that embody one or more of the equations discussed above that are used to calculate the carbon system parameters.

When it is desired to determine the measurable carbon system parameters of seawater, a seawater sample can be collected and its temperature (T) and salinity (S) can be measured. This can be performed, for example, using readily available, inexpensive temperature and salinity probes.

Subsamples of the collected seawater sample can then be added to the sample cells 16 of the spectrophotometer 12 for spectrophotometric analysis. As a first step in this analysis, the light absorbances of both subsamples can be measured with the spectrophotometer 12 at multiple visible wavelengths to obtain baseline light absorbances for the purpose of determining pH. Next, a pH indicator can be added to the first subsample and the light absorbances for the first subsample can again be measured at the same visible wavelengths. A ratio of the light intensities for the first subsample can be obtained in order to calculate absorbances, and absorbance ratios can then be used to calculate the pH of the first subsample (i.e., $pH_1$). In some embodiments, the measured light absorbances can be provided to the carbon system parameter program 32 for automatic calculation of $pH_1$ using a known algorithm.

Next, the UV light absorbances of the second subsample can be measured with the spectrophotometer at multiple UV wavelengths to obtain reference UV light absorbances. Once this is performed, an amount of nitric acid can be added to the second subsample as a titrant. As noted above because nitric acid inherently absorbs UV light and the concentration of added nitric acid can be determined based on the subsample's UV light absorbance, there is no need to add any indicator to the nitric acid. The UV light absorbances of the second subsample can again be measured at the same UV wavelengths after the addition of the nitric acid UV light absorbances can be then be used to determine the concentration of added nitric acid (i.e., $\Delta NO_3^-$) in the second subsample. In particular, UV absorbances can be correlated to a concentration once a calibration has been performed that correlates UV light absorbance ratios with concentrations of added nitric acid. In some embodiments, the measured UV light absorbances can be provided to the carbon system parameter program 32 for automatic determination of $\Delta NO_3^-$.

Once the $pH_1$ and $\Delta NO_3^-$ have been determined, the pH of the second subsample, $pH_2$, can be determined by adding a pH indicator to the second subsample and again measuring the light absorbances for the second subsample at visible wavelengths. A ratio of the light absorbances for the second subsample can be calculated from the measured visible light absorbances and this ratio can then be used to calculate the $pH_2$. As before, the visible light absorbances can be provided to the carbon system parameter program 32 for automatic calculation of $pH_2$.

As this point, $pH_1$, $pH_2$, and $\Delta NO_3^-$ have been obtained using spectrophotometric analysis. The dilution factor $\theta$ can also be determined through such analysis. In particular, $\theta$ can directly identified from the UV absorbance of the second subsample using a relationship identified in FIG. 3 and discussed below. Once $pH_1$, $pH_2$, $\Delta NO_3^-$, and $\theta$ are known, the above-described equations can be used to calculate total alkalinity ($A_T$), total dissolved inorganic carbon ($C_T$), the carbonate ion concentration ($[CO_3^{2-}]_T$), $CO_2$ fugacity ($fCO_2$), and carbonate saturation state ($\Omega$).

As can be appreciated from the above discussion, the procedures that are performed to determine the carbon system parameters are relatively simple and require neither expensive equipment nor great expertise.

Experimentation

Experiments were performed to evaluate the above describe method. Spectrophotometric measurements of $_{235}\varepsilon_{NO3}$ were made with a high-quality, dual-beam scanning spectrophotometer (Agilent Cary 400 Bio UV-VIS). Each time the Agilent Cary 400 is powered on, it performs an internal wavelength accuracy calibration by detecting the sharp emission lines of a deuterium lamp. The wavelength accuracy specification is ±0.08 nm. This large benchtop spectrophotometer was fitted with a custom-made 10 cm pathlength open-top quartz cell (Precision Cells, Inc.).

Spectrophotometric measurements of apparent nitrate molar absorptivity coefficients (described below) and $\Omega$ were made with less expensive, more portable diode array spectrophotometers suitable for fieldwork (Agilent model 8453). This instrument has a wavelength accuracy of ±0.5 nm. Two-port 10 cm cylindrical quartz cells (Starna Cells, Inc.) were used for all measurements. The four Agilent instruments used in this work are identified as spec1, spec2 (a and b), spec3 (a and b), and spec4. An a or b suffix (e.g., spec2a, spec2b) indicates wavelength recalibration: a indicates the state of the instrument before recalibration, and b indicates the state after recalibration.

For temperature control, all spectrophotometers were connected to a recirculating water bath (Lauda model E100) via insulated tubing, and a digital thermometer (ERTCO EUTECHNICS model 4400) was used to monitor solution temperature. A Guildline Portosal salinometer (model 8410) was used to measure seawater salinity, and Gilmont micrometer syringes (model GS-1200) were used to deliver liquid reagents.

Natural seawater collected from offshore surface waters of the Gulf of Mexico served as the sample matrix. Seawater filtrations were performed using 0.4 μm membrane filters (Nuclepore, Lot 81D5A4), and the filtered seawater was stored in a 50 L Nalgene container for later use. This container was sealed to prevent evaporation. Total alkalinity ($A_T$) of the seawater was measured spectrophotometrically following the procedure of Yao and Byrne (W. Yao, R. H. Byrne, Simplified seawater alkalinity analysis: Use of linear array spectrometers, Deep. Res. Part I Oceanogr. Res. Pap. 45 (1998) 1383-1392). An accuracy of better than ±2 μmol kg$^{-1}$ was confirmed using certified reference materials from the Scripps Institution of Oceanography. $A_T$ was re-measured periodically to verify the absence of changes attributable to dehydration. To achieve a range of experimental conditions for this work (i.e., seawater saturation states and pH), samples were bubbled with $CO_2$ gas.

The spectrophotometric pH measurements were conducted using meta-cresol purple (mCP) indicator (Aldrich, Lot 7005HH) and cresol red (CR) indicator (Biosynth, Lot 220307/11), both purified by flash chromatography. Nitric acid standardizations were conducted using unpurified phenol red (Acros Organics). Stock solutions of the indicators (10 mM) in sodium chloride solutions (0.7 M) were prepared using NaCl obtained from MP Biomedicals. Trace metal-grade nitric acid was obtained from Fischer Scientific and sodium carbonate (99.95%, extra pure, anhydrous) was obtained from Acros Organics. Anaerobe-grade carbon dioxide was obtained from Air Products and ultra-pure $N_2$ was obtained from Airgas.

The nitric acid was standardized by titration of sodium carbonate solutions, generally following the procedure outlined in Chapter 11 of Harris (D.C. Harris, Quantitative chemical analysis, W.H. Freeman and Co, 2010). Procedural modifications included the use of phenol red indicator (instead of bromocresol green), as well as the use of streaming nitrogen gas (instead of boiling) to purge the solution of $CO_2$.

All carbon system calculations were conducted using the Microsoft Excel program CO2SYS. The constants $K_1$ and $K_2$ were taken from Lueker et al. (T. Lueker, A. Dickson, C. Keeling, Ocean p$CO_2$ calculated from dissolved inorganic carbon, alkalinity, and equations for $K_1$ and $K_2$: validation based on laboratory measurements of CO2 in gas and, Mar. Chem. (2000)); KB was taken from Dickson (A. Dickson, Thermodynamics of the dissociation of boric acid in synthetic seawater from 273.15 to 318.15 K, Deep Sea Res. Part A. Oceanogr. Res. (1990)); $K_W$ was taken from Millero (F. Millero, Thermodynamics of the carbon dioxide system in the oceans, Geochim. Cosmochim. Acta. (1995)); $K_{sp}$ was taken from Mucci (A. Mucci, The solubility of calcite and aragonite in seawater at various salinities, temperatures, and one atmosphere total pressure, Am. J. Sci. (1983)); the bisulfate dissociation constant ($K_{HSO4}$) was taken from Dickson (A. G. Dickson, Standard potential of the reaction: AgCl(s)+1 2H2(g)=Ag(s)+HCl(aq), and the standard acidity constant of the ion HSO4– in synthetic sea water from 273.15 to 318.15 K, J. Chem. Thermodyn. 22 (1990) 113-127); and the dependence of BT on salinity was taken from Uppström (L. Uppström, The boron/chlorinity ratio of deep-sea water from the Pacific Ocean, Deep Res. Oceanogr. Abstr. (1974)).

The dilution factor θ of Eq. (3) was determined as a function of $_{235}A_{NO3}$ (using spec1). Spectrophotometric cells were filled with seawater and UV absorbances (235, 236, 237, 238, and 239 nm) were measured before and after additions of $HNO_3$ from a micrometer syringe. The resulting $\Delta NO_3^-$ range was 164.7<$\Delta NO_3^-$<553.0 μM. The initial volumes of seawater contained within the cells ($V_{SW}$) were determined by gravimetric calibration with Milli-Q® water. Volumes of added acid ($V_{HNO3}$) were obtained by weighing the syringe before and after each addition. A value of θ was then calculated (Eq. (3)) for each nitrate concentration, and linear regression was used to characterize θ as a function of $_{235}A_{NO3}$.

To determine the molar absorptivity of nitrate, the Cary 400 spectrophotometer was used to measure seawater absorbance at selected wavelengths over a range of nitrate concentrations. The wavelengths used were 235, 236, 237, 238, 239 (on the shoulder of the 225 nm nitrate absorbance peak) and 385 nm (a non-absorbing wavelength). These wavelengths were chosen to yield absorbance values appropriate for the range of experimental nitrate concentrations and the characteristics of the spectrophotometers and cell pathlengths being used. The absorbance measured at the non-absorbing wavelength, which was used to monitor and correct for potential baseline shifts, was maintained within ±0.002. The range of $\Delta NO_3^-$ was 335.0≤$\Delta NO_3^-$≤525.9 μM.

For each of these analyses, approximately 100 mL of filtered seawater was transferred to the open-top quartz cell, which was then placed into the Cary 400 spectrophotometer. Baseline absorbance measurements were taken at the six UV wavelengths, and five increments of nitric acid (0.477±0.001 M) were added to the seawater sample (approximately 70 μL for the first addition, with additions of 10 μL thereafter). Absorbances were remeasured after each addition. The amounts of added $HNO_3$ were determined by weighing the delivering syringe before and after each acid addition. The resulting five nitrate concentrations were then used in Eq. 4 to yield an average $_\lambda\varepsilon_{NO3}$ value for each absorbing wavelength. Solutions were maintained at 25° C.±0.1 throughout all experiments.

Nitrate molar absorptivity values were similarly obtained using the portable Agilent spectrophotometers spec2, spec3, and spec4, and these instrument-specific values are hereafter referred to as apparent molar absorptivities ($_\lambda\varepsilon_{NO3}*$). Absorbance measurements were made at 1 nm intervals between 235 and 239 nm and at 385 nm. The nitric acid concentration was 300±0.5 μM. Eq. (4) was used to calculate a $_\lambda\varepsilon_{NO3}*$ value for each instrument.

Each saturation state determination requires two spectrophotometric cells, each filled with a subsample of identical seawater. The first cell is used to measure the pH of the original seawater, and the second cell is used to measure the pH of the same seawater after the one-step addition of titrant (nitric acid). For these analyses, seawater was drawn directly from the 50 L storage container into the optical cells. Each cell was flushed with seawater for 20 seconds before being sealed with Teflon caps, then rinsed with tap water, dried with a paper towel, and placed in a custom-made cell warmer to thermally equilibrate to 25° C. In all analyses, cells were handled with a foam holder to minimize heat transfer. After thermal equilibration, the optical windows were wiped clean with a Kimwipe, and the cells were placed in the spectrophotometer for absorbance measurements.

For the first cell, the pH of the seawater sample ($pH_1$) was measured spectrophotometrically following the procedure of Clayton and Byrne (T. D. Clayton, R. H. Byrne, Spectrophotometric seawater pH measurements: total hydrogen results, Deep. Res. 40 (1993) 2115-2129), as summarized by standard operating procedure (SOP) 6b of Dickson et al. (A. Dickson, C. Sabine, J. Christian, Guide to best practices for ocean CO2 measurements (2007)). The indicator mCP was used for samples with $pH_1$>7.8, and CR was used for samples with $pH_1$<7.8. For mCP, absorbances were measured at 434, 578, and 730 nm; for CR, absorbances were measured at 433, 573, and 730 nm. The non-absorbing wavelength, 730 nm, was used to monitor and correct for baseline shifts. Two 10 μL additions of indicator were performed, and absorbance measurements were taken after each addition. This procedure provides corrections for the small pH perturbations created by indicator additions.

For the second (i.e., titrated) cell, UV absorbance measurements were first made to determine the amount of added acid, and then visible absorbance measurements were made to determine the final pH ($pH_2$) of the sample. First, a background absorbance measurement was taken at 235 nm and 385 nm. The cell was then acidified with a volume of $HNO_3$ sufficient to significantly depress the pH relative to $pH_1$, typically to ~7.2 but occasionally (i.e., when $pH_1$<7.8) to ~6.8. The amount of required $HNO_3$ ranged from 14 to 19 μL and was dependent on the value of $pH_1$. After acidification, the cell was manually mixed and then returned to the spectrophotometer's thermostated cell compartment. Absorbance measurements for the determination of $\Delta NO_3^-$ were taken at 235 nm and 385 nm, with $_{385}A$ being used for baseline corrections. Finally, $pH_2$ was measured using the same visible-absorbance protocol as was used for the first cell.

These paired sets of absorbance measurements were used to derive carbonate system parameters as outlined above. Values of $[H^+]_1$ and $[H^+]_2$ were calculated from $pH_1$ and $pH_2$. Values of $f_C$, $f_B$, and $f_W$ can be calculated directly from Eqs. (5), (6), and (7), but for convenience we used the program CO2SYS (which includes code to characterize the multiple dissociation constants as a function of S, T, and P). To obtain $f_B$ and $f_W$, we rely on the fact that these terms are a function of pH and are independent of $C_T$. The cell pH and an arbitrary $C_T$ value ($C_{T(A)}$) were supplied to CO2SYS as input parameters, along with the appropriate S, T, and P values. The resulting CO2SYS output included borate alkalinity and hydroxide alkalinity, which were then used in Eqs. (6) and (7) to obtain $f_B$ and $f_W$. To obtain $f_C$, CO2SYS was used to model a change in the inorganic carbon content of a hypothetical seawater sample at constant pH. Because $f_B$ and $f_W$ are constant at constant pH, any resulting change in $A_T$ can be attributed solely to $f_C$ (Eq. (8)). For each cell pH (i.e., $pH_1$ and $pH_2$), two different, arbitrary $C_T$ values (an initial value $C_{T(A)}$ and a final value $C_{T(B)}$) were specified as input parameters. From the resulting $A_T$ values ($A_{T(A)}$ and $A_{T(B)}$), a value of $f_C$ was calculated as the ratio of the change in $A_T$ to the change in $C_T$ at the specified pH:

$$f_{CX} = \frac{A_{T(B)} - A_{T(A)}}{C_{T(B)} - C_{T(A)}} \quad (14)$$

where X refers to $pH_1$ or $pH_2$.

With these values in hand, carbonate saturation states can be determined. Values of CT (obtained from Eq (12)) and $A_{T1}$ (obtained from Eq (8)) were input into CO2SYS (along with S, T, and P) to calculate aragonite saturation state ($\Omega_{spec}$). The accuracy of the $\Omega_{spec}$ measurements, $\Delta\Omega_{spec}$, was determined by comparing $\Omega_{spec}$ with conventionally calculated aragonite saturation states ($\Omega_{calc}$) obtained using the independently measured values of $A_{T1}$ (described above) and $pH_1$ (described above).

The relationship between dilution factor θ (Eq. (3)) and UV absorbance at 235 nm (a proxy for the concentration of added nitrate in a sample) is given by:

$$\theta 1 - 0.000776 \cdot {}_{235}A_{NO3} \quad (15)$$

The linear regression used to obtain this relationship is shown in FIG. 1. This equation is based on additions of 0.477 M $HNO_3$. For different concentrations of nitric acid, the slope will change by a factor of $0.477[HNO_3]^{-1}$. It is important to note that θ is a small correction factor in Eq. (12). In the present study, dilution corrections changed $A_{T1}$ and $C_T$ by 1-2 μmol kg$^{-1}$ and changed $\Omega_{spec}$ by ~0.005. In each case, the dilution correction is far smaller than the measurement imprecision.

Figure 3:
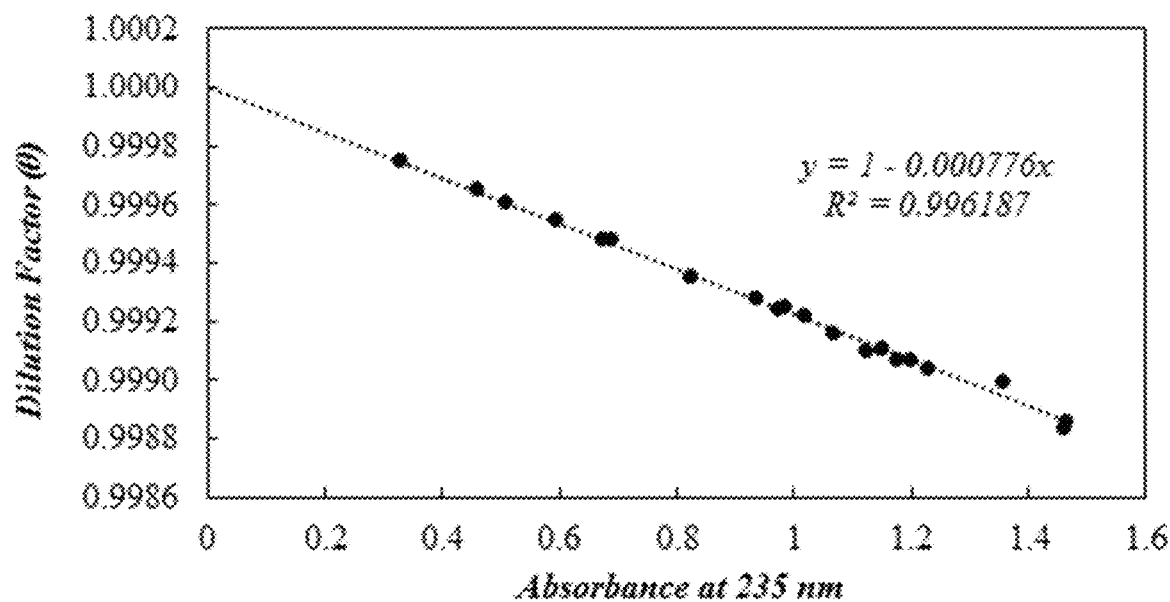
FIG. 3 is a graph that shows the relationship between the dilution factor $\theta$ and UV absorbance measured at 235 nm, using 10 cm cylindrical cells.

Nitrate molar absorptivity coefficients ($_\lambda\varepsilon_{NO3}$) measured on the Cary 400 Bio spectrophotometer at 1 nm intervals over the wavelength range 235-239 nm are presented in Table 1. The standard errors (1σ) of all $_\lambda\varepsilon_{NO3}$ values are <0.2%. The relationship between $\Delta NO_3^-$ and $_{235}A_{NO3}$ follows Beers Law, as expected (FIG. 3). These high-quality measurements are considered to represent actual nitrate molar absorptivity coefficients.

TABLE 1

| Wavelength (nm) | $\lambda\varepsilon_{NO3} \pm SE \cdot (cm^2 \cdot mole^{-1})^a$ |
|---|---|
| 235 | 276.6 ± 0.59 |
| 236 | 223.7 ± 0.40 |
| 237 | 180.4 ± 0.26 |
| 238 | 149.6 ± 0.14 |
| 239 | 118.9 ± 0.11 |

$^a$Average of 5 absorbance measurements at each wavelength

Apparent nitrate molar absorptivity coefficients measured on the portable Agilent spectrophotometers spec2, spec3, and spec4 at 235 nm are given in Table 2. All measurements were conducted at the same nitrate concentration, but the difference among the observed $_{235}A_{NO3}$ values obtained with different instruments was as large as 0.035. Because these coefficients are instrument-specific, we refer to them as apparent molar absorptivity coefficients, $_{235}\varepsilon_{NO3}^*$. For each spectrophotometer, these different values were tracked and used for all subsequent calculations. A value of $_{235}\varepsilon_{NO3}^*$ as not determined for spec1; all spec1-based calculations used the $_{235}\varepsilon_{NO3}$ value reported in Table 1. The differences between the Table 1 (actual) and Table 2 (apparent) molar absorptivities are due to sub-nanometer offsets in the wavelength calibrations of the Agilent instruments. When determining nitric acid concentrations via Eq. 4, $_{235}\varepsilon_{NO3}^*$ values specific to each instrument must be used.

TABLE 2

| Spectrophotometer$^a$ | $_{235}\varepsilon_{NO3}^{*\,b}$ |
|---|---|
| spec2a | 277.4 |
| spec2b | 288.0 |
| spec3a | 285.5 |
| spec3b | 274.0 |
| spec4 | 281.2 | a The a and b suffixes indicate determinations made before (a) and after (b) spectrophotometer recalibration.
b Values of $_{235}\varepsilon_{NO3}^*$ were calculated as the average value of five absorbance measurements.

In the accuracy assessments, any difference between $\Omega_{spec}$ and $\Omega_{calc}$ (where $\Delta\Omega_{spec}=\Omega_{spec}-\Omega_{calc}$) is considered to be a measurement error attributable to $\Omega_{spec}$. Values of $\Delta\Omega_{spec}$ greater than 3 standard deviations from the mean were considered to be outliers and were removed (3.3% of all $\Omega_{spec}$ measurements).

Figure 4:
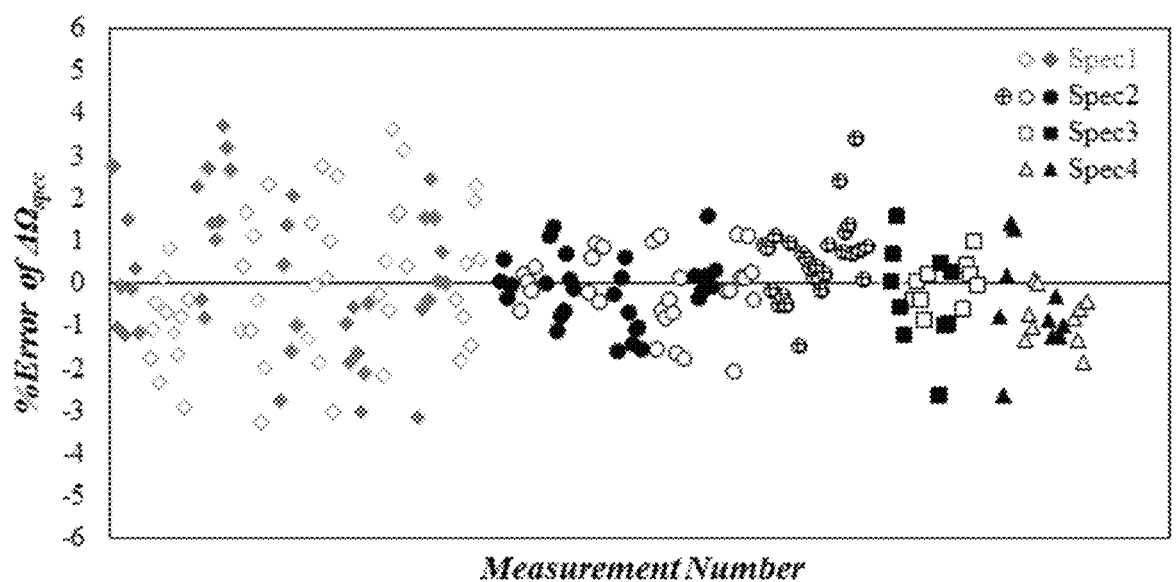
FIG. 4 is a graph that shows the percent error in aragonite saturation state measurements from the four portable Agilent spectrophotometers ($\Delta\Omega_{spec}=\Omega_{spec}-\Omega_{calc}$). The left-to-right alternating series of filled and empty symbols depict the different batches of measurements (29 batches, 212 total measurements).

FIG. 4 and Table 3 show the percent errors for aragonite saturation state measured with the four portable Agilent spectrophotometers. Table 3 also shows the range of experimental conditions. For spec1 (n=87), the errors center about zero (indicating that the wavelength calibrations of the Cary 400 and spec1 were fortuitously close); the mean and standard deviation of the percent errors are 0.05%±1.73%.

For spec2, spec3, and spec4 (combined n=125), the percent errors uniformly scatter about zero; the mean and standard deviation are −0.11%±0.96%. In FIG. 2, results for low-$\Omega$ seawater ($\Omega_{calc}$<1.18) are shown with textured circles, and those for high-$\Omega$ seawater ($\Omega_{calc}$>2.37) are shown in solid black; no samples fell into the intermediate $\Omega$ range. The corresponding ranges of $pH_1$ were 7.42-7.48 (low-$\Omega$ samples) and 7.84-8.03 (high-$\Omega$ samples).

TABLE 3

| Spectro-photometer[a] | n[a] | $\Omega_{calc}$ range | $\Omega_{spec}$ range | $\Delta\Omega_{spec}$[b] (average ± 1σ) | $\Delta\Omega_{spec}$ % error (average ± 1σ) |
|---|---|---|---|---|---|
| spec1 | 87 | 2.50-3.73 | 2.46-3.77 | 0.00 ± 0.05 | 0.05% ± 1.73% |
| spec2 high-$\Omega$ | 59 | 2.37-3.17 | 2.35-3.20 | −0.01 ± 0.02 | −0.18% ± 0.83% |
| spec2 low-$\Omega$ | 26 | 0.97-1.18 | 0.98-1.20 | 0.01 ± 0.01 | 0.56% ± 0.95% |
| spec3 | 20 | 3.03-3.17 | 3.01-3.11 | −0.01 ± 0.03 | −0.22% ± 0.92% |
| spec4 | 20 | 3.00-3.14 | 2.98-3.11 | −0.02 ± 0.03 | −0.65% ± 0.96% |

[a]n = number of measurements
[b]$\Delta\Omega_{spec} = \Omega_{spec} - \Omega_{calc}$ The measurements performed on spec1 exhibited significantly worse accuracy than measurements performed on the other three instruments (FIG. 4) due to a faulty (unstable) cell holder. Therefore, the discussions that follow refer exclusively to the measurements performed on spec2, spec3, and spec4.

Overall, 72% of the measured $\Omega_{spec}$ values were within 1% of the conventionally calculated saturation states, and 96% were within 2% of the calculated values. Estimates of $\Omega_{spec}$ precision are given as the combined standard deviation (1σ) of replicate measurements. For the pool of measurements obtained using spec2, spec3, and spec4, the $\Omega_{spec}$ precision was 0.020. Relative standard uncertainty (RSU) values were also obtained from the mean (μ) and standard deviation (σ) of batches of replicate measurements (RSU=σμ$^{-1}$*100). Overall, 90% of the measurements had RSUs<1%, and all measurements had RSUs<2%.

Figure 5:
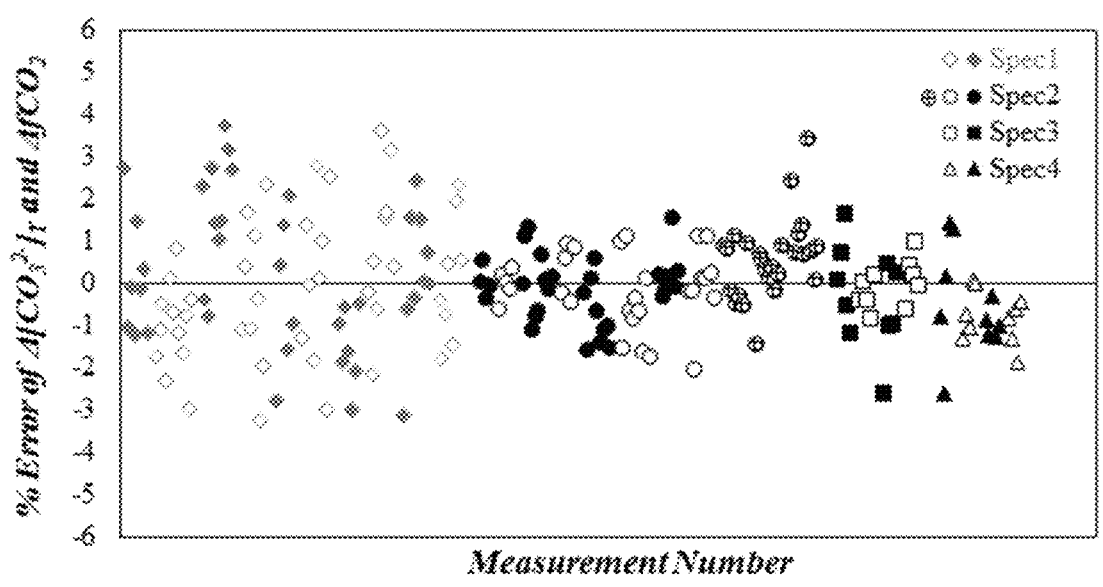
FIG. 5 is a graph that shows the percent errors in $[CO_3^{2-}]_{TSpec}$ and $fCO_{2spec}$ determinations derived from absorbance measurements on the four portable spectrophotometers ($\Delta X_{spec}=X_{spec}-X_{calc}$). The left-to-right alternating series of filled and empty symbols depict the different batches of measurements (29 batches, 212 total measurements).

For each seawater sample, carbonate ion concentration and $CO_2$ fugacity were also calculated from the spectrophotometrically determined values of $C_T$ (Eq. (12)) and $A_{T1}$ (Eq. 8)). FIG. 5 shows the percent errors for $[CO_3^{2-}]_{Tspec}$ and $fCO_{2spec}$. For spec2, spec3, and spec4, the measurements included high carbonate concentrations ($[CO_3^{2-}]_{Tcalc} \geq 147.1$ μmol kg$^{-1}$, in the high-$\Omega$ samples) and low carbonate concentrations ($[CO_3^{2-}]T_{calc} \leq 75.6$ μmol kg$^{-1}$, in the low-$\Omega$ samples). Values of $fCO_{2calc}$ ranged from 416 μatm (high-$\Omega$ samples) to 2073 μatm (low-$\Omega$ samples). Table 4 presents the average and standard deviation of the $[CO_3^{2-}]T_{spec}$ and $fCO_{2spec}$ residuals for each sample type.

TABLE 4

Accuracy of $[CO_3^{2-}]_{Tspec}$ and $fCO_{2spec}$ measurements (n = 125)

| | $\Delta[CO_3^{2-}]_{Tspec}$ (average ± 1σ) | $\Delta fCO_{2spec}$ (average ±1σ) |
|---|---|---|
| High-$\Omega$ seawater[a] 147.1 < $[CO_3^{2-}]_{Tcalc}$ < 198.8 μmol kg$^{-1}$ 416 < $fCO_{2calc}$ < 658 μatm | −0.5 ± 1.6 μmol kg$^{-1}$ | −1.3 ± 4.3 μatm |
| Low-$\Omega$ seawater[b] 61.2 < $[CO_3^{2-}]_{Tcalc}$ < 75.6 μmol kg−1 1803 < $fCO_{2calc}$ < 2073 μatm | 0.4 ± 0.6 μmol kg$^{-1}$ | 11.1 ± 18.9 μatm |

[a]High-$\Omega$ seawater is defined as $\Omega$calc > 2.37
[b]Low-$\Omega$ seawater is defined as $\Omega$calc < 1.18

FIG. 5 shows that, like the $\Omega_{spec}$ measurements, 72% of the $[CO_3^{2-}]_{Tspec}$ and $fCO_{2spec}$ measurements were within 1% of the values calculated from the $pH_1$-$A_T$ measurements, and 96% were within 2% of the calculated values. RSU values for the $[CO_3^{2-}]_{Tspec}$ measurements were also similar to the RSUs obtained for $\Omega_{spec}$: 90% of the $[CO_3^{2-}]_{Tspec}$ measurements had RSUs<1%, and all had RSUs<2%. For $fCO_{2spec}$, 26% of the measurements had RSUs<1%, and 54% had RSUs<2%.

The results in FIGS. 4 and 5 and Tables 3 and 4 are based on single samples. The extent to which improvements in precision and accuracy might be realized by using averages obtained from duplicate samples was also assessed. Specifically, values of $\Omega_{spec}$, $[CO_3^{2-}]_{Tspec}$, and $fCO_{2spec}$ were calculated from average values of $C_T$ (Eq. (12)) and $A_{T1}$ (Eq. (8)) obtained from duplicate seawater samples.

For $\Omega_{spec}$, the combined, duplicate-based (spec2, spec3, and spec4) mean and standard deviation of the percent errors were −0.11%±0.73% (compared to −0.11%±0.96% for the single-sample errors); the 95% confidence interval (CI) was ±1.3% (down from ±2.0% for the single-sample measurements). The precision of $\Omega_{spec}$ improved from 0.020 to 0.014. The percentage of measurements with RSUs <1% increased from 90% (single samples) to 97% (duplicate samples), and all duplicate-based $\Omega_{spec}$ measurements had RSUs <1.4%.

For $[CO_3^{2-}]_{Tspec}$ and $fCO_{2spec}$, the duplicate-based mean and standard deviation of the percent errors were −0.11%±0.73% (compared to −11%±0.96% for the single-sample errors); the 95% CI for the duplicate-based measurements was ±1.3% (down from ±2.0% for the single-sample measurements). The RSUs for the duplicate-based $[CO_3^{2-}]_{Tspec}$ measurements were similar to those for sp: the percentage of measurements with RSUs<1% increased from 90% (single samples) to 97% (duplicate samples), and all duplicate-based $[CO_3^{2-}]_{Tspec}$ measurements had RSUs<1.4%. For the duplicate-based $fCO_{2spec}$ measurements, the percentage of measurements with RSUs<1% increased from 26% (single samples) to 78%, and 97% had RSUs<2% (up from 54% for the single-sample measurements).

Discussion

The foregoing disclosure documents the accuracy and precision that can be achieved for calcium carbonate saturation state determinations obtained solely via spectrophotometry. Sulfonephthalein indicator absorbances at visible wavelengths are used to precisely quantify the pH of natural and acidified seawater samples. After a single-step titration with nitric acid, the direct (Beers Law) relationship between nitrate concentration and UV absorbance is used to quantify the acid:seawater mixing ratio. Using this protocol, the need for gravimetric or volumetric measurements to quantify amounts of added acid is eliminated and the only instrumentation required is a standard spectrophotometer. The measurements are simple and convenient, and each measurement is obtained in about 12 minutes. The utilization of nitric acid for titrations increases the simplicity and speed of the saturation state determinations without causing substantial loss of precision and accuracy.

The Global Ocean Acidification Observing Network (GOA-ON) has formulated accuracy goals that serve as useful metrics for assessing the utility of seawater carbonate system measurements, based on the relative standard uncertainty of the measurements. GOA-ON data that achieve the "weather level" accuracy goals can be used to assess short-term spatial and temporal patterns and to help interpret ecosystem responses to localized OA dynamics; data that achieve the more demanding "climate level" goals can be used to assess long-term anthropogenically driven changes in carbon chemistry.

For our single-sample $\Omega_{spec}$ and $[CO_3^{2-}]_{Tspec}$ measurements, 100% of the measurements exhibited RSUs<2%, which is well within the GOA-ON "weather level" accuracy goals of RSU<10%. Moreover, 90% of these measurements achieved the "climate level" accuracy goals of RSU<1%. The 10% of the measurements that did not achieve the climate goal were made in low-$\Omega$ waters (where $\Omega_{calc}$<1.18 and $[CO_3^{2-}]_T$<75.6 µmol kg$^{-1}$). For our fCO$_{2spec}$ samples, 92% of the measurements achieved the "weather level" accuracy goal of RSU<2.5%. However, only 4% of these measurements achieved the "climate level" goal of RSU<0.5%.

Performance of this method can be improved by using average $C_T$ and $A_{T1}$ values (Eqs. (12) and (8)) obtained from measurements of duplicate samples. For $\Omega_{spec}$ and $[CO_3^{2-}]T_{spec}$, this additional effort would not be justified if "weather level" accuracy is the aim because this goal is already achieved 100% of the time through single-sample measurements. However, if long-term "climate level" monitoring is the goal, then the significant gains achieved through duplicate measurements becomes important. Using the duplicate-sample approach, 97% of our $\Omega_{spec}$ and $[CO_3^{2-}]T_{spec}$ measurements achieved the "climate level" goals of accuracy (up from 90% for the single-sample approach). In addition, the percentage of fCO$_{2spec}$ measurements that achieved the "weather level" goal increased to 96% (previously 92%) and the percentage that reached the "climate level" goal increased to 32% (previously 4%). Running duplicate samples doubles the measurement time required to 24 minutes per sample, but the increases in precision and accuracy may be beneficial and even essential in some circumstances.

FIG. 4 illustrates how the accuracy of the $\Omega_{spec}$ method may be improved through operator care and experience. The scatter of $\Delta\Omega_{spec}$ values associated with spec1 were substantially larger than the scatter associated with spec2, spec3, and spec4. The source of the disparity was, in part, a somewhat uneven spec1 cell compartment that caused comparatively large baseline shifts (>0.006) for the absorbance measurements. Another contributing factor could be that the spec1 data were from the earliest experiments, and operator skill (i.e., sample handling) likely improved through time. The smaller standard deviations of the spec2, spec3, and spec4 data likely provide a better representation of the achievable precision of this method.

If $\Omega_{spec}$ determinations are made using a Cary 400 or comparable spectrophotometer, then the value of $_{235}\varepsilon_{NO3}$ reported in Table 1 can be used directly in Eq. (4) to provide accurate $\Omega_{spec}$ values without further calibration. However, if $\Omega_{spec}$ determinations are made using an Agilent 8453 or comparable spectrophotometer, then user-determined instrument-specific apparent molar absorptivity coefficients ($_{235}\varepsilon_{NO3}*$) must be used. Small deviations in wavelength calibrations between spectrophotometers (±0.1 nm) can create large deviations in measured absorbances and, thereby, large errors in $\Omega_{spec}$. The use of instrument-specific $_\lambda\varepsilon_{NO3}*$ values eliminates the problems associated with these small wavelength discrepancies. Whenever an instrument's wavelength scale is recalibrated, a new $_{236}\varepsilon_{NO3}*$ must be determined for that instrument (as illustrated in Table 2). The procedure for determining $_{235}\varepsilon_{NO3}*$ is given in the supplementary material. It is important to emphasize that after a one-time, instrument-specific characterization of $_{235}\varepsilon_{NO3}*$, the disclosed spectrophotometric method to determine carbonate saturation state is calibration-free. In addition, it is important to note that subnanomolar differences in wavelength calibrations are insignificant for spectrophotometric pH determinations because those absorbance measurements are made at the broad absorbance maxima of sulfonephthalein indicators.

The choice of which sulfonephthalein indicator to use for the pH absorbance measurements (mCP or cresol red) is crucial for accurate $\Omega_{spec}$ determinations. When pH$_1$>7.8, mCP must be used; when pH$_1$<7.8, CR is recommended. The choice of an indicator therefore requires some upfront knowledge of the likely seawater pH. The pH of most coastal and open ocean waters is >7.8, so most measurements will utilize mCP. Cases where CR would likely be used include coastal upwelling regions, deep-water samples, and areas where microbial respiration is high.

The efficacy (precision or resolution) of the spectrophotometric saturation state measurements described in this work depend in large part on achieving a substantial difference between pH$_1$ and pH$_2$. However, the extent to which large pH differences can be measured spectrophometrically is limited by the small suite of well-characterized purified indicators. Currently, only mCP (pK~8.0; [19]) and CR (pK~7.8) meet the requisite criteria. Using larger nitric acid additions or more concentrated nitric acid in order to achieve pH2<6 would likely significantly improve the precision and accuracy of the $\Omega_{spec}$ measurements. Implementation of this advancement, though, will require (a) thorough characterization of a lower-pK indicator (e.g., bromocresol purple, pK~5.8) and (b) determination of $_\lambda\varepsilon_{NO3}*$ at longer wavelengths to compensate for the larger absorbance values that would result from higher concentrations of nitric acid.

The spectrophotometric procedure developed in this work is also amenable to in situ applications. Because the mixing ratio of seawater and nitric acid is determined spectrophotometrically, the need for accurate volumetric metering of acid delivery is eliminated. The achievable in situ precision is directly dependent on the accuracy of the spectrophotometric measurements. Notably, because a single spectrophotometric cell would be used for any in situ analyses, absorbance errors associated with the manual manipulation of spectrophotometric cells (i.e., moving cells into and out of the spectrophotometers) would be eliminated, thereby improving $\Omega_{spec}$ precision and accuracy relative to benchtop measurements. The development of procedures for in situ analysis will, of course, require characterization of the temperature and pressure dependencies of nitrate molar absorptivities.

Seawater carbonate saturation state determinations that require only spectrophotometric instrumentation, which is widely available and relatively inexpensive, creates new opportunities for simple, fast, and cost-effective monitoring of ocean acidification. Spectrophotometric measurements of saturation state are especially suitable for applications where the highest achievable precision and accuracy are not required. Potential applications include observations in coastal areas (where spatial and temporal variability are high) as well as the routine monitoring of seawater at fish hatcheries and shellfish farms.

While the above disclosure has focused on seawater, it is noted that the systems and methods described herein can be adapted for use with freshwater. Accordingly, the scope of the disclosure is not intended to be limited to seawater alone.

The invention claimed is:
1. A method for determining carbon system parameters of water, the method comprising:

measuring a pH of a first subsample of the water using a spectrophotometer;

adding nitric acid as a titrant to a second subsample of the water to obtain a titrated subsample;

measuring a concentration of added nitric acid in the titrated subsample using a spectrophotometer;

measuring a pH of the titrated subsample using a spectrophotometer; and calculating total alkalinity of the water using the pH of the first subsample, the pH of the titrated subsample, and the concentration of added nitric acid in the titrated subsample.

2. The method of claim 1, wherein measuring the pH of the first subsample and measuring the pH of the titrated subsample comprises measuring light absorbances of the subsamples at visible wavelengths.

3. The method of claim 1, wherein measuring the concentration of added nitric acid in the titrated subsample comprises measuring light absorbances of the titrated subsample at ultraviolet wavelengths.

4. The method of claim 3, wherein no indicator is added to the nitric acid to measure the light absorbances of the titrated subsample.

5. The method of claim 1, wherein total alkalinity is calculated using a computer program configured for that purpose.

6. The method of claim 1, further comprising calculating a total dissolved inorganic carbon of the water.

7. The method of claim 6, further comprising measuring a salinity and temperature of the water.

8. The method of claim 7, further comprising calculating a carbonate ion concentration of the water using the total alkalinity, the total dissolved inorganic carbon, the salinity, and the temperature of the water.

9. The method of claim 8, further comprising calculating a carbon dioxide fugacity of the water.

10. The method of claim 8, further comprising calculating a carbonate saturation state of the water using the carbonate ion concentration of the water.

11. The method of claim 1, wherein the water is seawater.

12. A system for determining carbon system parameters of water, the system comprising:

a spectrophotometer configured to measure light absorbances of liquids; and a computing device in communication with the spectrophotometer, the computing device including a non-transitory computer-readable medium that stores a carbon system parameter program configured to:

receive spectrophotometric absorbance measurements indicative of a pH of an untitrated subsample of the water, receive spectrophotometric absorbance measurements indicative of a pH of a subsample of the water that has been titrated with nitric acid, receive spectrophotometric absorbance measurements indicative of a concentration of added nitric acid in the titrated subsample, determine a pH value for each subsample and a concentration of added nitric acid in the titrated subsample from the spectrophotometric absorbance measurements, and calculate total alkalinity of the water using the pH values and the concentration of added nitric acid in the titrated subsample of the water.

13. The system of claim 12, wherein the carbon system parameter program is configured to calculate the total alkalinity of the water and a total dissolved inorganic carbon of the water using the pH values and the concentration of added nitric acid in the titrated subsample of the water.

14. The system of claim 13, wherein the carbon system parameter program is further configured to calculate carbonate ion concentration of the water using the total alkalinity, total dissolved inorganic carbon, salinity, and temperature of the water.

15. The system of claim 14, wherein the carbon system parameter program is further configured to calculate carbonate saturation state of the water using the carbonate ion concentration of the water.

16. A computer-readable medium that stores a carbon system parameter program, the program being configured to:

receive spectrophotometric absorbance measurements indicative of a pH of an untitrated subsample of water, receive spectrophotometric absorbance measurements indicative of a pH of a subsample of the water that has been titrated with nitric acid, receive spectrophotometric absorbance measurements indicative of a concentration of added nitric acid in the titrated subsample, determine a pH value for each subsample and a concentration of added nitric acid in the titrated subsample from the spectrophotometric absorbance measurements, and calculate total alkalinity of the water using the pH values and the concentration of added nitric acid in the titrated subsample of the water.

17. The computer-readable medium of claim 16, wherein the carbon system parameter program is configured to calculate the total alkalinity of the water and a total dissolved inorganic carbon of the water using the pH values and the concentration of added nitric acid in the titrated subsample of the water.

18. The computer-readable medium of claim 17, wherein the carbon system parameter program is further configured to calculate a carbonate ion concentration of the water using the total alkalinity, total dissolved inorganic carbon, salinity, and temperature of the water.

19. The computer-readable medium of claim 18, wherein the carbon system parameter program is further configured to calculate a carbonate saturation state of the water using the carbonate ion concentration of the water.

* * * * *